(12) United States Patent
Dwyer et al.

(10) Patent No.: US 8,690,921 B2
(45) Date of Patent: *Apr. 8, 2014

(54) INTERSPINOUS INTERNAL FIXATION/DISTRACTION DEVICE

(75) Inventors: James W. Dwyer, Neshanic Station, NJ (US); John Murphy, Chester, NJ (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/493,630

(22) Filed: Jun. 11, 2012

(65) Prior Publication Data

US 2012/0245639 A1    Sep. 27, 2012

Related U.S. Application Data

(63) Continuation of application No. 11/461,610, filed on Aug. 1, 2006, now Pat. No. 8,221,462.

(60) Provisional application No. 60/704,268, filed on Aug. 1, 2005.

(51) Int. Cl.
*A61B 17/70* (2006.01)

(52) U.S. Cl.
USPC .......................................... 606/249; 606/248

(58) Field of Classification Search
USPC .................................................. 606/246–279
See application file for complete search history.

(56) References Cited

U.S. PATENT DOCUMENTS

| | | | | |
|---|---|---|---|---|
| 5,645,599 A | * | 7/1997 | Samani | 623/17.16 |
| 6,048,342 A | * | 4/2000 | Zucherman et al. | 606/249 |
| 6,402,750 B1 | * | 6/2002 | Atkinson et al. | 606/279 |
| 6,451,019 B1 | | 9/2002 | Zucherman et al. | |
| 2005/0010293 A1 | * | 1/2005 | Zucherman et al. | 623/17.11 |
| 2005/0203512 A1 | * | 9/2005 | Hawkins et al. | 606/61 |
| 2005/0245937 A1 | * | 11/2005 | Winslow | 606/90 |

* cited by examiner

*Primary Examiner* — Jerry Cumberledge
*Assistant Examiner* — Nicholas Plionis

(57) ABSTRACT

Disclosed are an apparatus for an interspinous fixation and/or distraction of vertebrae and a methodology for minimally invasive implantation of the apparatus in the spine of a patient. The apparatus corresponds to a pair of teardrop shaped lateral wing elements spaced apart by a central core element that may be selectively sized during the implantation process. The wings and central core are held together by a single threaded bolt and locking nut configuration resulting in a simple structure that may be easily implanted with minimal patient discomfort.

17 Claims, 2 Drawing Sheets

INTERSPINOUS INTERNAL FIXATION/DISTRACTION DEVICE

CROSS REFERENCE TO RELATED APPLICATIONS

This patent application is a continuation application claiming priority to U.S. patent application Ser. No. 11/461,610, filed on Aug. 1, 2006 now U.S. Pat. No. 8,221,462, which claims priority to U.S. Provisional Application 60/704,268, filed Aug. 1, 2005, the entire contents of which are incorporated by reference herein in their entireties.

FIELD OF THE INVENTION

The present technology relates to an interspinous fixation, and/or distraction device designed for minimally invasive implantation in the spine. More particularly, the present technology relates to an apparatus that may be implanted by herein disclosed methodologies in the lumbar area of the spine of a patient.

BACKGROUND OF THE INVENTION

The spinal column is a bio-mechanical structure principally composed of vertebrae and intervertebral disks, along with ligaments, muscles, collectively whose primary functions may be regarded as including support of the body as well as protection of the spinal cord and associated nerve roots. The spinal column's body support functionality involves distribution of weight from the various extremities and the torso to the pelvis and legs. As individuals age, various adverse spinal column conditions may develop that often result in back pain. Non-limiting examples of such conditions include spinal stenosis, thickening of spinal column constituent bones, facet antropathy, facet joint arthritis, facet synovial cyst, annular tear, painful disc disruption, and segmental instability.

Currently, pain originating from such conditions (and others) may be treated with medications and/or surgically. However, it is often the case that at present, in severe circumstances, such treatment requires invasive surgical correction. A principle goal for any such surgical correction should be to minimize or eliminate the need for major surgery in all patients and, most especially, for elderly patients.

Accordingly, to address such defective spinal column conditions and others, there is need to develop devices and methodologies that are minimally invasive and that can be well tolerated by all patients, especially elderly patients.

Prior efforts to address such spinal column conditions have resulted in the development of some forms of interspinous implants for implantation between adjacent spinous processes for the relief of pain associated with the spine. One such device is described in U.S. Pat. No. 6,695,842 to Zucherman et al., entitled "Interspinous Process Distraction System and Method With Positionable Wing and Method" with an issue date of Feb. 24, 2004. Such Zucherman et al. device includes a central spacer and a pair of end wings in a complex configuration including a fastener with a tapered head. The tapered head cooperates with a similarly tapered cavity portion of one of the wings to provide adjustment of the one wing relative to the other wing.

A similar device is described in US Patent Application Publication US 2004/0181282 A1 to Zucherman et al., entitled "Interspinous Process Apparatus and Method With A Selectably Expandable Spacer" with a publication date of Sep. 16, 2004. The device disclosed in such '282 publication is similar to that of the previously mentioned '842 patent but provides a selectably expandable spacer that, by adjusting a screw mechanism, can be adjusted in place. The Zucherman et al. '282 published patent application, like the '842 patent, suffers the same inherent complexity issues. In addition, from a surgery management perspective, the potential need to access such adjusting screw mechanism has the potential for requiring additional invasive procedures on the patient.

While various implementations of implantable interspinous internal fixation/distraction devices have been developed, no design has emerged that generally encompasses all of the desired characteristics as hereafter presented in accordance with the subject technology.

BRIEF SUMMARY OF THE INVENTION

In view of the recognized features encountered in the prior art and addressed by the present subject matter, a present broad object is to provide for improved interspinous fixation and/or distraction with minimally invasive implantation in the spine. In the same context, it is a present object to provide improved, minimally invasive interspinous implants, developed so that they may be implanted through a relatively small incision (for example, such as 1-2") in a manner such that the presently disclosed implant remains safely outside the spinal canal. In such manner, a further present object is achieved for thereby desirably avoiding any potential neurological injury or late epidural scarring.

Additionally, various of presently disclosed implants, when used in accordance with the present methodology, may be implanted using local or IV conscious sedation, with the patient positioned in a standard prone position, thereby allowing same day outpatient surgery and rapid ambulation. Thus, another present object is to provide generally for improved surgical-based treatments for certain defective spinal conditions of patients.

Per further present objects, exemplary implant devices in accordance with the present technology function to stabilize the motion segment in distraction through the posterior elements. Such present methodology and approach advantageously results in increased spinal canal area and diameter, increased foraminal height and area, unloading of facet joint contract forces, unloading of posterior annulus, and degreased intra-discal pressure.

The potential positive clinical effects for some patients of implantation of the device in accordance with the present technology is decreased radicular, leg pain by improved neural element compression in the upright position and to decreased mechanical back pain by decreased loading of facet joints and posterior annulus structures. In such manner, the present implant devices per present methodology, advantageously act as an internal splint or brace for spinal structures.

In an exemplary configuration, implants in accordance with the present technology are provided with a pair of wings for lateral translation fixation, and provided with a central core element for longitudinal fixation and distraction. In accordance with aspects of some embodiments of the present subject matter, the diameter of the central core element may be selected at the time of implant surgery from a number of pre-constructed elements, based on spacing requirements determined either before or during the time of an actual surgical procedure.

In accordance with aspects of certain, additional embodiments of the present subject matter, methodologies and apparatus have been developed that facilitate repeated assembly, disassembly, and reassembly of an exemplary present device during the implantation process so as to facilitate fine-tuned sizing of the device even after initial implantation. Such facility may be imparted in an exemplary form of the present subject matter through the provision of a single bolt and locking nut design that secures in place all components of subject exemplary implant and provides mechanical integrity to the finally assembled device.

In accordance with certain aspects of other embodiments of the present subject matter, methodologies and apparatus have been developed to facilitate implantation of the subject device in a pre-assembled form or, alternatively, in a modular fashion as necessary or as convenient during implantation surgery.

Additional objects and advantages of the present subject matter are set forth in, or will be apparent to, those of ordinary skill in the art from the detailed description herein. Also, it should be further appreciated that modifications and variations to the specifically illustrated, referred and discussed features, elements and/or steps hereof may be practiced in various embodiments and uses of the present subject matter without departing from the spirit and scope of the present subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which.

Figure 1:
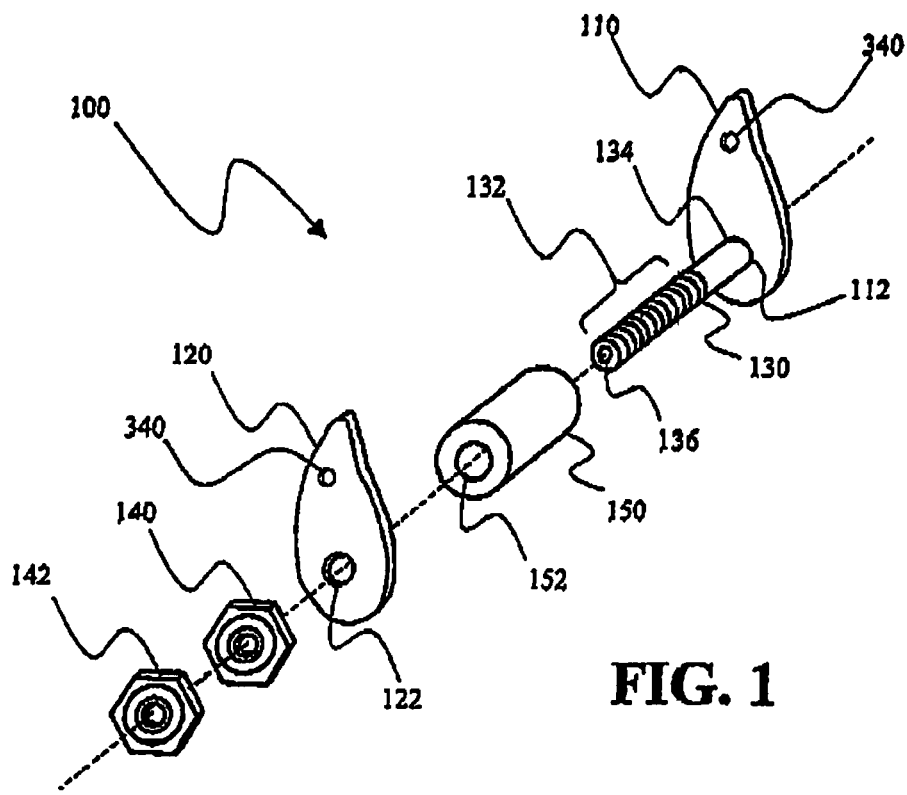
FIG. 1 is an exploded view of an exemplary interspinous implant device in accordance with the present technology, to show its exemplary component parts.

Repeat use of reference characters throughout the present specification and appended drawings is intended to represent same or analogous features, elements or steps of the present subject matter.

DETAILED DESCRIPTION OF THE INVENTION

As discussed in the Brief Summary of the Invention section, the present subject matter is particularly concerned with interspinous fixation and/or distraction devices designed for minimally invasive implantation in the spine, particularly, but not exclusively, in the lumbar area of the spine. It should be clearly understood that although the principle portion of the present disclosure is directed to apparatus and methodologies for implantation of such apparatus in the lumbar area of the spine, such disclosure is not meant to be a limitation on the present subject matter as the apparatus and methodologies disclosed herein may also be associated with other areas of the spine.

Selected combinations of aspects of the disclosed technology correspond to a plurality of different embodiments of the present subject matter. It should be noted that each of the exemplary embodiments presented and discussed herein should not insinuate limitations of the present subject matter. Features or steps illustrated, described or suggested (either literally or as discerned by one of ordinary skill in the art) as part of one embodiment may be used in combination with aspects of another embodiment or embodiments to yield yet further embodiments. Additionally, certain features may be interchanged with similar devices or features not expressly mentioned or shown, which perform the same or similar function.

Reference will now be made in detail to the presently preferred embodiments of the subject interspinous implantable devices and corresponding associated methodologies. Referring now to the drawings, FIG. 1 is an exploded view illustrating the component parts of an exemplary embodiment of a subject interspinous internal fixation/distraction device generally 100. As shown, devise 100 includes by way of example a pair of lateral wings 110 and 120. In this instance, such lateral wings may be preferably teardrop-shaped, and may be coupled together by way of an exemplary threaded bolt 130 and lock nut 140, 142 configuration.

In the exemplary embodiment generally 100, a central core element (generally 150) is receivable over exemplary threaded bolt 130 by virtue of its illustrated central through bore 152. Threaded bolt 130 may be threaded along a significant portion of one end thereof (see generally exemplary region 132 shown in FIG. 1), to accommodate secure fixation of various lengths and diameters of core element 150, as will be more fully described herein.

The other end (generally 134) of threaded bolt 130 may be press fit or otherwise secured into a hole 112 in a relatively lower portion of teardrop shaped wing 110. It should be appreciated that end 134 of threaded bolt 130 may be secured to wing 110 in any suitable manner. Non-limiting examples of other methods of securement, in addition to the previously mentioned press fitting, may include welding, gluing, threaded engagement, or providing a head on end 134 of threaded bolt 130. It is also possible per the present subject matter to machine wing 110 and threaded bolt 130 from a single piece of material.

Nuts 140, 142 may be threaded onto the threaded portion 132 of threaded bolt 130 after passing threaded bolt 132 through hole 122 formed in the relatively lower portion of teardrop shaped wing 120.

Figure 2:
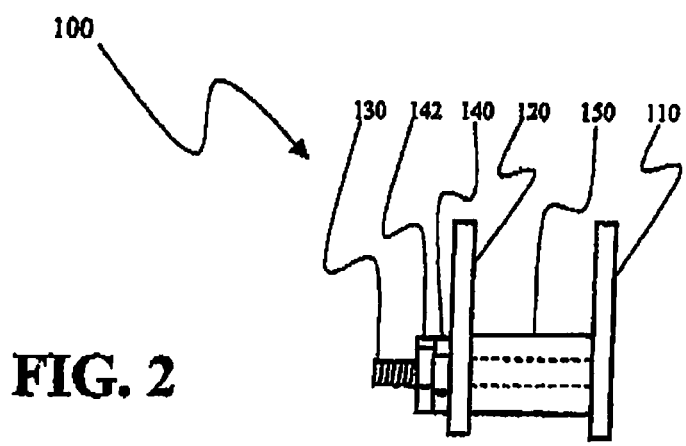
FIG. 2 is a side elevation of a fully assembled exemplary present implant device.

The foregoing arrangement collectively serves to secure the various components in assembled fashion, as illustrated in side view in FIG. 2.

The threaded end portion 132 of threaded bolt 130 may preferably contain a small pilot hole 136, the function of which will be further explained herein with respect to the device implantation process. A similar pilot hole (not seen in the FIG. 1 view) may be provided in the opposite end 134 of threaded bolt 132. Alternatively, such pilot hole 136 may extend through the entire length of the threaded bolt 132.

All of the various exemplary components corresponding in assembled form to device 100 as illustrated in representative FIGS. 1 and 2 may advantageously be constructed of biocompatible materials. Non-limiting examples of such materials include stainless steel, titanium, high molecular weight polyethylene (HMWPE), and polyetherether-Ketone (PEEK™, a high performance engineering thermoplastic resin manufactured by Victrex, plc.). Titanium may be advantageously employed to allow optimum postoperative imaging while PEEK™ may be advantageous in selected circumstances as it mimics the modulus of elasticity of bone.

It is, of course, not necessary that all components of an exemplary present embodiment be made of the same materials. For example, wings 110, 120, threaded bolt 130 and nuts 140, 142 may be made of titanium to obtain the benefit of improved postoperative imaging while central core 150 may be made of PEEK™ for its bone mimicking modulus of elasticity. It should be clearly borne in mind that these specific examples are non-limiting to the present technology as materials from which a particular device of the present technology may be constructed may be chosen for a number of reasons and may depend, in part, on specific situations unique to any one patient's particular requirements. In fact, the present technology may be practiced using not only the previously mentioned materials but also with as yet undeveloped materials as the exact nature of the specific materials used is not critical to the present technology in its broadest forms.

Figure 3:
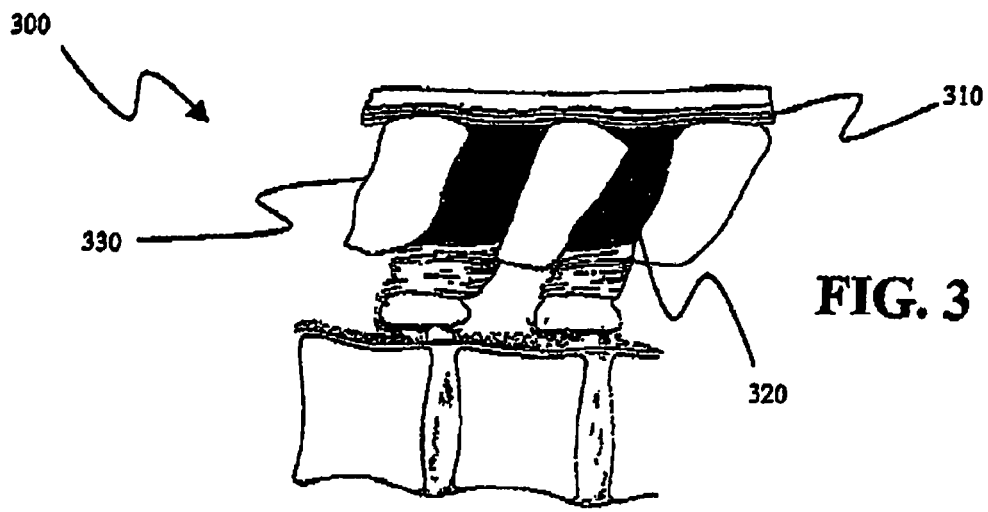
FIG. 3 illustrates a portion of a lumbar section of a patient's spine, to illustrate exemplary conditions in which the present technology may be applied.

With reference now to FIG. 3, there is illustrated a side elevational view of a representative lumbar section 300 of an exemplary patient's spine to which the present technology may be applied. Particular note is taken of the interspinous ligament 310, the supraspinous ligament 320, and the spinous process generally 330.

Figure 4:
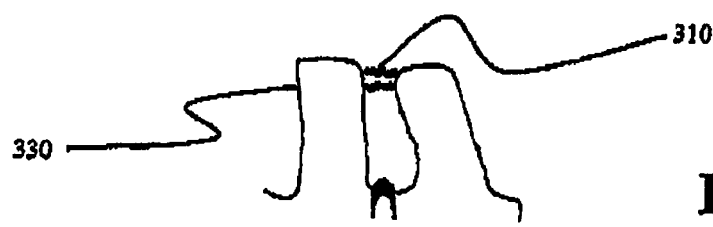
FIGS. 4, 5 and 6 respectively are schematic representations of an exemplary sequence of steps for implanting an exemplary present device according to the present methodology.
Figure 5:
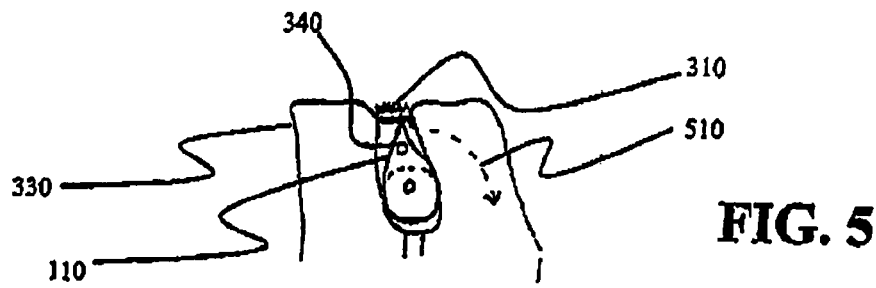
Figure 6:
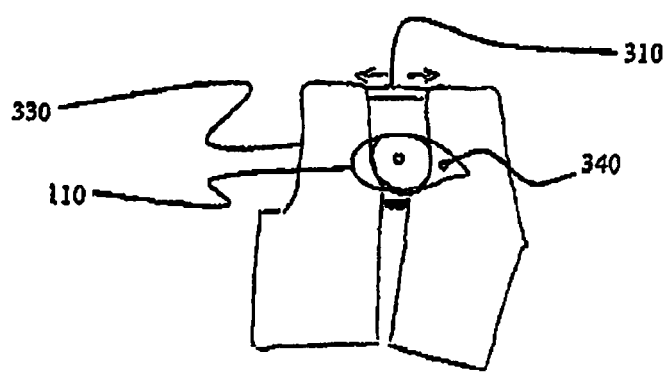

With reference now to FIGS. 4, 5 and 6, there is shown a sequence of respective illustrations demonstrating an exemplary methodology for implanting an exemplary device 100 in accordance with the present technology. Because of its modularity and unique design, exemplary device 100 can be implanted via a relatively small (for example, about 1-2") unilateral incision in the dorsolumbar fascia with the patient positioned in the standard prone position. Current and previous devices have often required more extensive (and thus, more painful) bilateral fascia and muscle incisions. Such occurrences result disadvantageously in greater soft tissue disruption, increased pain, increased blood loss, and larger scars. Some of the current devices require surgery to be performed with the patient in a decubitus (lateral) position. Such position often results in prolonged surgical time, and secondarily in difficulty with intraoperative x-ray imagining as well as decreased surgeon familiarity with the requisite surgical approach.

With further reference to FIGS. 4, 5 and 6, an exemplary surgical procedure with respect to implanting exemplary device 100 in accordance with the present technology will be generally described.

FIG. 4 illustrates the pre-operative condition of the illustrated lumbar section portion of the representative spine 300 to be addressed during the present surgical procedure. After surgically exposing the spinous processes 330, the interspinous ligament 310 and the supraspinous ligament 320 (FIG. 3) are identified. A blunt probe may be used to create an entry portal through the interspinous ligament 310. The substantially completely assembled device 100 may then be inserted through the interspinous ligament 310 to the opposite side.

The term substantially completely assembled is meant to convey the concept that, during surgery, the central core element 150 may be swapped out with variously sized such elements to achieve optimal fine tuning of the implant prior to final positioning of the lock nuts 140, 142 into locking engagement. As is explicitly illustrated in representative present FIG. 5, the exemplary device 100, due in part to the low profile, teardrop configuration of wings 110, 120, may be inserted substantially fully assembled between the spinous processes 330. The teardrop design conforms to lamina, broad surface area and provides optimal medial lateral stabilization and fixation.

If positioning of the device 100 is now in the optimal transverse lie, then the small pilot hole 136 in the central shaft of threaded bolt 130, using, for example, a micro-lever device, can be used to tune the wings 110, 120 (following the direction of arrow 510; see FIG. 5) into optimal position, as illustrated in FIG. 6. Such rotation into optimal position can be accomplished with device 100 fully assembled or with wing and threaded bolt separately assembled. With reference to FIG. 6, it will be observed that upon rotation of wings 110, 120 into optimal position for lateral retention of assembled device 100, the posterior supraspinous ligament 320 will be tightened and taut as a secondary aspect to the distraction and stabilization of the spinous processes 330. Threaded openings (see representative openings 340 in FIGS. 1, 5, and 6) provided in proximal and distal wing elements in accordance with the present subject matter allow for screw fixation (or equivalent) to the spinous process. Such feature maintains optimal position to maintain distraction and to avoid unintended displacement.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. An implant comprising:
    a body comprising a central core member extending between a first wing portion and a second wing portion, the core member comprising a bore for receiving a bolt therethrough;
    wherein the first wing portion is fixed to one end of the bolt;
    wherein the bolt extends through the bore of the core member and through the second wing portion;
    wherein a nut is positioned on the bolt after passing the bolt through the second wing portion to secure the second wing portion to the core member;
    wherein the second wing portion is threaded onto a threaded portion of the bolt; and
    wherein a pilot hole is configured in a central shaft of the bolt and wherein the pilot hole extends throughout the bolt for receiving a lever device for rotating the wing portions from a first position to a second position.

2. The implant of claim 1, wherein the core member is generally cylindrical.

3. The implant of claim 1, wherein the first wing portion is generally tear-dropped shaped.

4. The implant of claim 1, wherein the core member is made of polyetheretherketone (PEEK).

5. The implant of claim 1, wherein the first wing portion and the second wing portion are formed of PEEK.

6. The implant of claim 1, wherein the first wing portion and the second wing portion are laterally spaced by a distance generally corresponding to a predetermined distance for accommodating the width of a spinous process.

7. The implant of claim 1, wherein the core member is made from titanium.

8. An implant comprising:
   a body comprising a central core member extending between a first wing portion and a second wing portion, the core member comprising a bore for receiving a bolt therethrough;
   wherein the bolt extends through the bore of the core member and through the second wing portion;
   wherein a nut is positioned on the bolt after passing the bolt through the second wing portion to secure the second wing portion to the core member;
   wherein the first and second wing portions are threaded onto threaded portions of the bolt; and
   wherein a pilot hole is configured in a central shaft of the bolt and wherein the pilot hole extends throughout the bolt for receiving a lever device for rotating the first wing portion and the second wing portion.

9. The implant of claim 8, wherein the first wing portion and the second wing portion are generally tear-dropped shape.

10. The implant of claim 8, wherein an upper portion of the first wing portion and an upper portion of the second wing portion comprise second holes.

11. The implant of claim 10, wherein the second holes are configured to accommodate a fastening device to fasten the implant to the spinous process.

12. The implant of claim 8, wherein the first and second wing portions are configured to contact lateral sides of a spinous process when the implant is positioned in a vertebral column.

13. An implant comprising:
   a body comprising a central core member extending between a first wing portion and a second wing portion, the core member comprising a bore for receiving a threaded bolt therethrough;
   wherein the first wing portion is fixed to one end of the threaded bolt;
   wherein the threaded bolt extends through the bore of the core member and through the second wing portion;
   wherein a nut is positioned on the threaded bolt after passing the threaded bolt through the second wing portion to secure the second wing portion to the core member; and
   wherein an upper portion of the first wing portion and an upper portion of the second wing portion comprise second holes, wherein the second holes are configured to accommodate a fastening device to fasten the implant to a spinous process.
   wherein a pilot hole is configured in a central shaft of the bolt and wherein the pilot hole extends throughout the threaded bolt for receiving a lever device for rotating the wing portions from a first position to a second position.

14. The implant of claim 13, wherein the first wing portion is tear-dropped shape.

15. The implant of claim 13, wherein the central core member is generally cylindrical.

16. The implant of claim 13, wherein the implant comprises first and second nuts positioned on the bolt for securing the second wing portion to the core member.

17. The implant of claim 13, wherein the first wing portion and the second wing portion are laterally spaced by a distance generally corresponding to a predetermined distance for accommodating the width of a spinous process.

* * * * *